United States Patent [19]

Dietz et al.

[11] Patent Number: 4,937,345
[45] Date of Patent: Jun. 26, 1990

[54] PROCESS FOR THE PREPARATION OF 2-(ARYLAMINO)-3-CARBOXY-9(10H)-ACRIDONES

[75] Inventors: Erwin Dietz, Kelkheim; Heinrich Hamal, Liederbach; Frank Prokschy, Frankfurt am Main, all of Fed. Rep. of Germany

[73] Assignee: Hoechst Aktiengesellschaft, Frankfurt am Main, Fed. Rep. of Germany

[21] Appl. No.: 254,365

[22] Filed: Oct. 6, 1988

[30] Foreign Application Priority Data

Oct. 10, 1987 [DE] Fed. Rep. of Germany ....... 3734383

[51] Int. Cl.$^5$ ............................................. C07D 219/08
[52] U.S. Cl. ...................................... 546/103; 546/49
[58] Field of Search ........................................ 546/103

[56] References Cited

U.S. PATENT DOCUMENTS

| | | | |
|---|---|---|---|
| 3,257,405 | 6/1966 | Gerson et al. | 546/49 |
| 3,342,823 | 9/1967 | Dien et al. | 546/49 |
| 4,544,746 | 10/1985 | Höltje | 546/103 |

FOREIGN PATENT DOCUMENTS 1382259 1/1975 United Kingdom .

*Primary Examiner*—Diana G. Rivers

[57] ABSTRACT

A process for the preparation of 2-(arylamino)-3-carboxy-9(10H)-acridones of the formula A

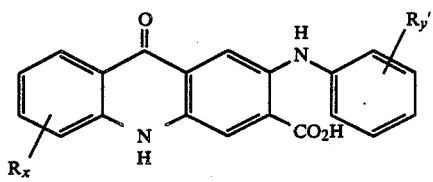

in which R and R' represent hydrogen, fluorine, chlorine or bromine atoms, alkyl($C_1$–$C_4$)-, oxalkyl($C_1$–$C_4$)- or carbonamide groups and x and y denote integers from 1 to 4, by cyclizing 2,5-diarylaminoterephthalic acids of the formula D

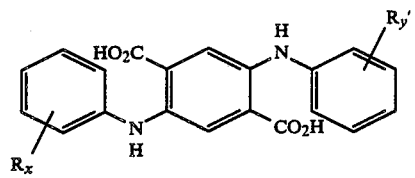

in which R, R', x and y have the meanings mentioned previously, in a 5- to 15-fold amount by weight of polyphosphoric acid ($P_4O_{10}$ content 80 to about 85%) or of an acidic polyphosphate ($P_4O_{10}$ contents 75 to about 85%) as a water-abstracting agent at about 60° C. to about 100° C.

8 Claims, No Drawings

PROCESS FOR THE PREPARATION OF 2-(ARYLAMINO)-3-CARBOXY-9(10H)-ACRIDONES

DESCRIPTION

The present invention relates to an improved process for the preparation of 2-(arylamino)-3-carboxy-9(10H)-acridones (2-arylamino-acridone-3-carboxylic acids) of the general formula A

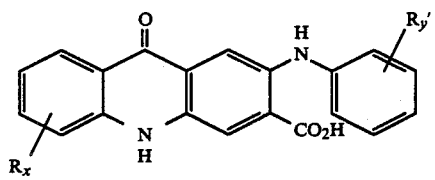

in which R and R' represent hydrogen, fluorine, chlorine or bromine atoms, alkyl($C_1$-$C_4$)-, oxalkyl($C_1$-$C_4$)- or carbonamide groups and x and y denote integers from 1 to 4, in a water-abstracting, acidic medium at moderately high temperatures.

Compounds of the said general formula -A or the corresponding alkyl carboxylates are important precursors for the preparation of 2-(arylamino)-9(10H)-acridones of the general formula B (U.S. Pat. Nos. 4,544,746, 4,258,190) and for quinacridones of the general formula C (DE-OS 2,165,647)

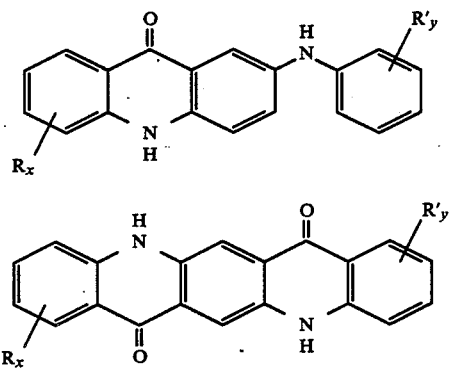

in which R, R', x and y have the previously mentioned meanings.

Compounds of the said general formula B- are used as mixed crystal components for improving the light- and weather-fastness of quinacridonequinone pigments (US-PS 4,286,998); quinacridones of the said general formula -C have great significance as pigments in the most diverse areas of use.

A process for the preparation of the hitherto unknown 2-arylamino-acridone-3-carboxylic acids has already been described in DE-OS 2,165,647 or GB-PS 1,382,259, in which 3,6-dihydro-2,5-diarylaminoterephthalates are cyclized under suitable conditions to the corresponding 1,4-dihydro-2-arylamino-acridone-3-carboxylates, these are then dehydrogenated to the corresponding acridones and these are in turn hydrolyzed to compounds of the general formula A. The disadvantage of this process lies in the low yields of the compounds A (50-60 %, relative to the dihydroterephthalic acid derivative).

In U.S. Pat. No. 4,544,746, the synthesis of the compounds of the said general formula A from the 2,5-diarylaminoterephthalic acids of the general formula D starts out according to the reaction equation

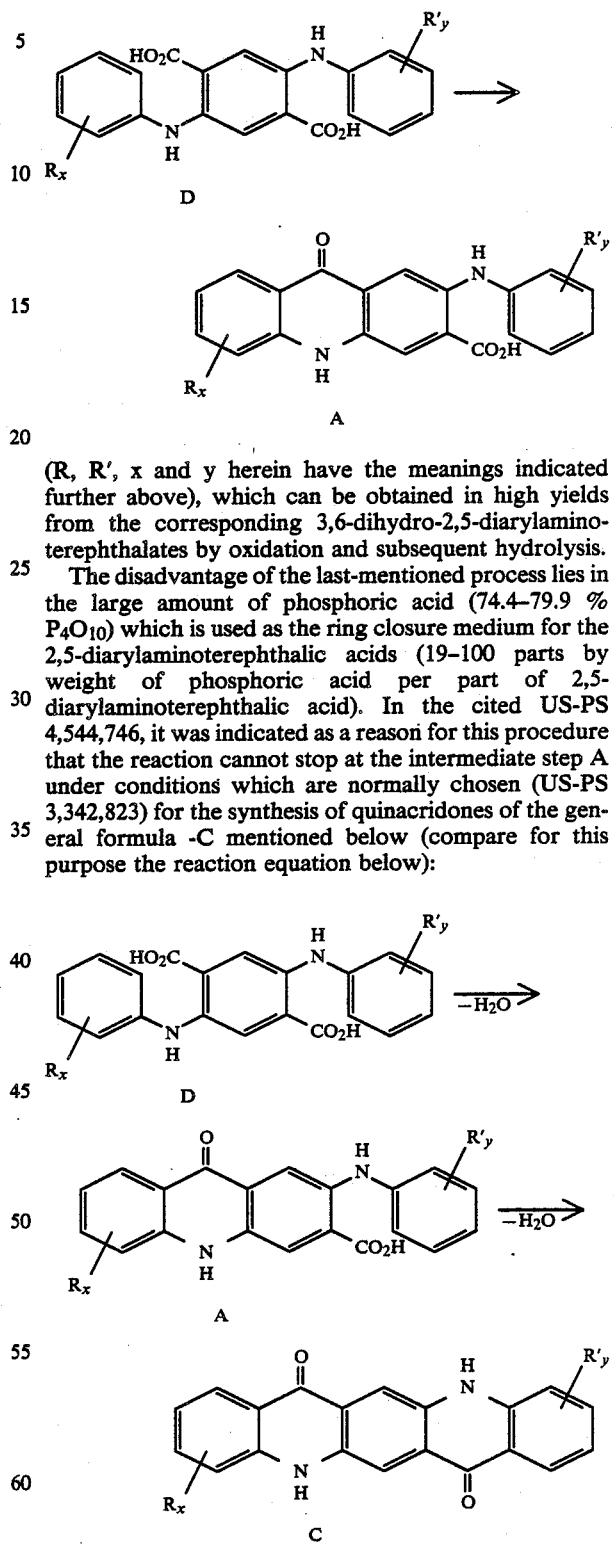

(R, R', x and y herein have the meanings indicated further above), which can be obtained in high yields from the corresponding 3,6-dihydro-2,5-diarylaminoterephthalates by oxidation and subsequent hydrolysis.

The disadvantage of the last-mentioned process lies in the large amount of phosphoric acid (74.4-79.9 % $P_4O_{10}$) which is used as the ring closure medium for the 2,5-diarylaminoterephthalic acids (19-100 parts by weight of phosphoric acid per part of 2,5-diarylaminoterephthalic acid). In the cited US-PS 4,544,746, it was indicated as a reason for this procedure that the reaction cannot stop at the intermediate step A under conditions which are normally chosen (US-PS 3,342,823) for the synthesis of quinacridones of the general formula -C mentioned below (compare for this purpose the reaction equation below):

In view of the great significance of the compounds of the said general formula (A) or their carboxylates as precursors for the compounds of the said general formulae B and C and owing to the said serious disadvantages of the processes known from DE-OS 2,165,647

(GB-PS 1,382,259) or US-PS 4,544,746, a considerable need existed for a better process which avoids the said disadvantages of the known processes.

It has now surprisingly been found that 2-(arylamino)-3-carboxy-9(10H)-acridones of the general formula A

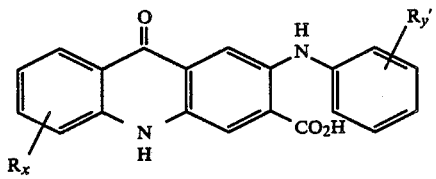

in which R and R' represent hydrogen, fluorine, chlorine or bromine atoms, alkyl($C_1$–$C_4$)-, oxalkyl($C_1$–$C_4$)- or carbonamide groups and x and y denote integers from 1 to 4, can be prepared with high yields in an advantageous manner by cyclizing 2,5-diarylaminoterephthalic acids of the general formula D

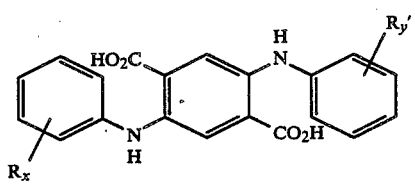

in which R, R', x and y have the said meanings, in a 5- to 15-fold, preferably 5- to 8-fold, amount by weight of polyphosphoric acid ($P_4O_{10}$ content 80 to about 85 %), or of an acidic polyphosphate ($P_4O_{10}$ content 75 to about 85 %, preferably 78 to 82 %) as a water-abstracting agent at temperatures of about 60° C. to about 100° C., preferably about 80° C. to about 90° C.

Suitable acidic polyphosphates are principally the methyl, benzyl and phenyl esters.

It appears that the cyclization of the compounds of the formula D to the compounds of the formula -A first proceeds relatively rapidly under the conditions used.

In order to facilitate the work-up, the reaction is continued until no starting compound of the formula D is any longer present which, however, has the consequence that the compounds of the formula A obtained can react in low amounts to give the compounds of the formula -C.

The reaction procedure in general takes place in such a way that the 2,5-diarylaminoterephthalic acids of the said general formula -D are introduced at reaction temperature into the ring closure medium. The course of the reaction is followed by thin-layer chromatography. The end of the reaction is reached when no 2,5-diarylaminoterephthalic acid is any longer present in the batch. The time of reaction depends essentially on the temperature and the ring closure medium (water-abstracting agent) used. Certain contents of quinacridones of the said general formula C- can also be detected in the reaction product, the amount of which is dependent on the reaction temperature and the type of ring closure medium (water-abstracting agent). The isolation of these likewise useful compounds takes place in the manner which is customary for the separation of an acidic from a neutral organic compound and is also described in US-PS 4,544,746, namely by treating the mixture with an aqueous alkali metal hydroxide solution. During the course of this, the acidic compound of the formula -A goes into solution, whereas the compound of the formula -C is separated by filtration. The filtrate is subsequently acidified, the compound of the formula A precipitating.

The process according to the invention for the preparation of the compounds of the formula -A from the compounds of the formula D advantageously differs from the process known from US-PS 4,544,746, in that on the one hand it is carried out at lower temperatures, and on the other hand a substantially lower ratio of ring closure medium to 2,5-diarylaminoterephthalic acid (formula -D) is used, which has ecological advantages.

The amounts indicated in the examples below are amounts by weight; the percentage data are percent by weight.

EXAMPLES

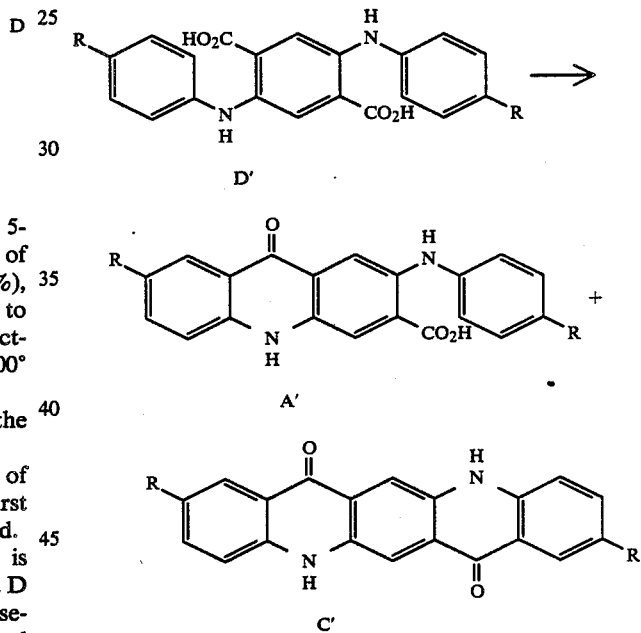

a parts of polyphosphoric acid (PPA) or acidic methyl polyphosphate (MePP) are warmed to 70°–75° C. with the content of $P_4O_{10}$ indicated; subsequently b parts of 2,5-diarylaminoterephthalic acid are introduced in x hours in such a way that T (see table below) is not exceeded; the reaction batch is then stirred for a further y hours at temperature T.

Hydrolysis takes place by pouring the batch into c parts of water at 80° C. Subsequently, the hydrolyzate is stirred for a further 1–2 hours at 80°–90° C. After filtering off with suction, washing and drying, d parts of a mixture which predominantly consists of 2-arylamino-acridone-3-carboxylic acid of the formula A' containing a low content of quinacridone of the formula C' are obtained.

The previously described reaction forms the basis of the Table Examples 1 to 14 below.

| Example | R | a | PPA AND MePP | % P$_4$O$_{10}$ | T | b | x | y | c | d | %A' | %C' |
|---|---|---|---|---|---|---|---|---|---|---|---|---|
| 1 | H | 1200 | PPA | 80.7 | 85° C. | 200 | 1.5 | 1 | 3600 | 180 | 91.6 | 8.4 |
| 2 | H | 800 | PPA | 85.0 | 85° C. | 100 | 0.5 | 3 | 4000 | 89 | 75 | 25 |
| 3 | H | 1200 | PPA | 81.4 | 85° C. | 200 | 3 | 1 | 3600 | 181 | 84 | 16 |
| 4 | H | 1030 | PPA | 80.0 | 80° C. | 172 | 2 | 4 | 3100 | 160 | 93.3 | 6.7 |
| 5 | H | 1200 | PPA | 80.8 | 85° C. | 200 | 2 | 1 | 3600 | 180 | 96.3 | 3.7 |
| 6 | H | 1200 | PPA | 81.7 | 85° C. | 200 | 2.75 | 1 | 3600 | 180 | 87 | 13 |
| 7 | H | 600 | MePP | 78.5 | 85° C. | 100 | 2 | 1 | 1800 | 92 | 76 | 24 |
| 8 | H | 150 | MePP | 81.8 | 85° C. | 25 | 0.5 | 1 | 500 | 22 | 79 | 21 |
| 9 | H | 250 | MePP | 78.1 | 83° C. | 42 | 0.25 | 4 | 750 | 38 | 84 | 16 |
| 10 | CH$_3$ | 1200 | PPA | 80.7 | 80° C. | 200 | 1 | 3.25 | 3600 | 180 | 94 | 6 |
| 11 | CH$_3$ | 1200 | PPA | 82.3 | 80° C. | 200 | 1.5 | 3 | 3600 | 186 | 91 | 9 |
| 12 | CH$_3$ | 150 | MePP | 78.9 | 85° C. | 25 | 0.25 | 1 | 500 | 23 | 84 | 16 |
| 13 | Cl | 200 | MePP | 78.5 | 87° C. | 20 | 0.5 | 7 | 600 | 17 | 45 | 55 |
| 14 | Cl | 500 | PPA | 80.7 | 90° C. | 100 | 1.25 | 5 | 1500 | 38 | 77 | 23 |

If, instead of the amounts of acidic methyl polyphosphate indicated in the preceding table, those amounts of acidic benzyl or phenyl polyphosphates are so that the percentage content of P$_4$O$_{10}$ of these esters is identical, then the compounds of the formula A' are obtained in satisfactory yields.

The separation of the quinacridone from the mixture takes place in such a way that the moist filter cake, which is obtained after filtering off with suction and washing the hydrolyzate neutral, is stirred into the 35-fold amount by weight (relative to the dry weight) of water, adjusted to a pH of 12 using 30% strength sodium hydroxide solution and stirred for 2 hours at a temperature of 60° C. The mixture is subsequently filtered off with suction and the residue is washed, the quinacridone of the formula C' being obtained. The corresponding 2-arylamino-acridone-3-carboxylic acid of the formula A' is obtained from the mother and wash liquors after adjusting to a pH of 4 by means of acetic acid, filtering off with suction, washing and drying.

Similar results are obtained when, as starting compounds of the formula D', those are employed in which R denotes an ethyl group or a fluorine or bromine atom.

We claim:

1. A process for the preparation of 2-(arylamino)-3-carboxy-9(10H)-acridones of the general formula A

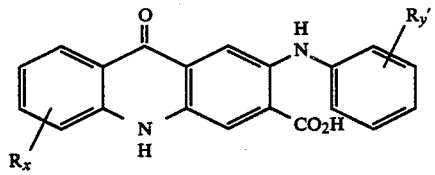

in which R and R' represent hydrogen, fluorine, chlorine or bromine atoms, alkyl(C$_1$–C$_4$)-, oxalkyl(C$_1$–C$_4$)or carbonamide groups and x and y denote integers from to 4, which comprises cyclizing 2,5-diarylaminoterephthalic acids of the general formula D

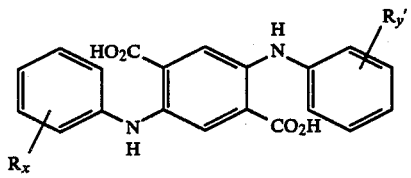

in which R, R', x and y have the meanings mentioned previously, in a 5- to 15-fold amount by weight of polyphosphoric acid (P$_4$O$_{10}$ content 80 to about 85 %) or of an acidic polyphosphate (P$_4$O$_{10}$ content 75 to about as a water-abstracting agent at temperatures of about 60° C. to about 100° C.

2. The process as claimed in claim 1, wherein cyclization takes place at temperatures of about 80° C. to about 90°.

3. The process as claimed in claim 1, wherein the cyclization takes place in a 5- to 8-fold amount by weight of polyphosphoric acid or of an acidic polyphosphate.

4. The process as claimed in claim 1 wherein the cyclization takes place in the presence of an acidic polyphosphate having a P$_4$O$_{10}$ content of 78 to 82 %.

5. The process as claimed in claim 1 wherein a compound of the general formula D, in which R and/or R' denote the methyl or ethyl group or a fluorine, chlorine or bromine atom, is cyclized.

6. A process for the preparation of essentially a 2-(arylamino)-3-carboxy-9(10H)acridone compound of the general formula A

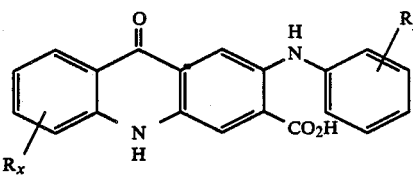

in which R and R' represent hydrogen, fluorine, chlorine or bromine atoms, alkyl(C$_1$–C$_4$)-, oxalkyl(C$_1$–C$_4$)- or carbonamide groups and x and y denote integers from 1 to 4, which comprises (a) cyclizing, at a temperature within the range of about 60° to about 100° C., 2,5-dairylaminoterephthalic acids of the general formula D

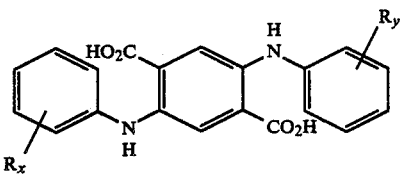

in which R, R', x and y have the meanings defined above, in a 5- to 15-fold amount by weight of polyphosphoric acid (P$_4$O$_{10}$ content 80 to about 85%) or of an acidic polyphosphate (P4010 content 75 to about 85%) as essentially the water-abstracting agent for the cyclization reaction, and (b) recovering said compound of formula A as the major product of the cyclization reaction.

7. The process as claimed in claim 6, wherein the acidic polyphosphate with the $P_4O_{10}$ content of 75 to about 85% is a methyl, benzyl, or phenyl ester of the polyphosphoric acid.

8. The process as claimed in claim 6, wherein a minor amount of quinacridine is formed, and said compound of formula A is recovered and separated from the quinacridone by dissolving said compound of formula A in solution, separating the quinacridone by filtration, and then precipitating said compound of formula A from the solution.

* * * * *

UNITED STATES PATENT AND TRADEMARK OFFICE
CERTIFICATE OF CORRECTION

PATENT NO. : 4,937,345

DATED : 6/26/90

INVENTOR(S) : ERWIN DIETZ, ET AL.

It is certified that error appears in the above-identified patent and that said Letters Patent is hereby corrected as shown below:

In the Abstract;
In Col. 1, line 12;
In Col. 3, line 9;
In Claim 1, Col. 5, line 43; and
In Claim 6, Col. 6, line 38, at the right-hand side of formula A, "Ry'" should read -- R'y --.

In the Abstract;
In Col. 3, line 25;
In Claim 1, Col. 5, line 57;
In Claim 6, Col. 6, line 54, at the right-hand side of formula A, "Ry'" should read -- R'y --.

In Col. 3, line 35, "P4O10" should read -- $P_4O_{10}$ --.

In Claim 1, Col. 5, line 68, please insert -- 85%) -- after "about",

In Claim 6, Col. 6, line 50, "2, 5-dairylaminotereph-" should read -- 2, 5-diarylaminotereph- --.

UNITED STATES PATENT AND TRADEMARK OFFICE
CERTIFICATE OF CORRECTION

PATENT NO. : 4,937,345

DATED : 6/26/90

INVENTOR(S) : ERWIN DIETZ, ET AL.

It is certified that error appears in the above-identified patent and that said Letters Patent is hereby corrected as shown below:

In Claim 6, Col. 6, line 64, "P4O10" should read -- $P_4O_{10}$ -- .

In Claim 8, Col. 7, line 6, "quinacridine" should read -- quinacridone -- .

Signed and Sealed this

Twenty-ninth Day of October, 1991

Attest:

HARRY F. MANBECK, JR.

*Attesting Officer*     *Commissioner of Patents and Trademarks*